United States Patent [19]

Marconi et al.

[11] 4,396,716

[45] Aug. 2, 1983

[54] PREPARATION OF BIOCOMPATIBLE MATERIALS BY IMMOBILIZATION OF APYRASE

[75] Inventors: Walter Marconi, S. Donato Mi; Francesco Bartoli; Francesco Pittalis, both of Rome, all of Italy

[73] Assignee: E.N.I. Ente Nazionale Idrocarburi, Rome, Italy

[21] Appl. No.: 334,907

[22] Filed: Dec. 28, 1981

Related U.S. Application Data

[63] Continuation of Ser. No. 165,708, Jul. 3, 1980, abandoned.

[30] Foreign Application Priority Data

Aug. 1, 1979 [IT] Italy ............................. 24838 A/79

[51] Int. Cl.³ ..................... C12N 11/06; C12N 11/08; A61F 1/00
[52] U.S. Cl. ........................................... 435/181; 3/1; 435/180
[58] Field of Search ............... 435/174, 176, 177, 180, 435/181; 3/1

[56] References Cited

U.S. PATENT DOCUMENTS 3,705,084  12/1972  Reynolds ........................... 435/180
3,865,915  2/1975  Manly ................................... 3/1 X
4,273,873  6/1981  Sugitachi et al. .................... 435/180

OTHER PUBLICATIONS

Patel et al., In Soluble Matrix-Supported Apyrase, Deoxyribonuclease and Cholinesterase Biochim. Biophys. Acta, vol. 178, 1969, (pp. 626–629).
Gaarder et al., Adenosine Diphosphate in Red Cells as a Factor in the Adhesiveness of Human Blood Platelets, Nature, vol. 192, 1961, (pp. 531–532).

*Primary Examiner*—David M. Naff
*Attorney, Agent, or Firm*—Morgan, Finnegan, Pine, Foley & Lee

[57] ABSTRACT

A prosthetic polymer material is made non-thrombogenic by immobilizing apyrase on its surface. Immobilization is preferably carried out by hydrolytically activating the surface of a polyamide polymer or a polyethylene terphthalate polymer, and treating the hydrolyzed polymer with a solution of cross-linking agent and a solution of apyrase. The apyrase converts adenosine diphosphate to adenosine monophosphate and adenosine whereby the formation of thrombi is inhibited.

4 Claims, No Drawings

PREPARATION OF BIOCOMPATIBLE MATERIALS BY IMMOBILIZATION OF APYRASE

The present application is a continuation of application Ser. No. 165,708 filed July 3, 1980, now abandoned.

This invention relates to a process for preparing biocompatible polymer and non-polymer materials by immobilising apyrase on their surface, apyrase being an enzyme able to catalyse the conversion of adenosine diphosphate (ADP) to adenosine monophosphate (AMP), followed by the conversion of this latter to adenosine. The invention also relates to the manufactured articles obtained by said process.

The possibility of imparting biocompatible properties to various types of material is of enormous practical importance at the present time. In this respect, materials exist which because of their good mechanical, machining and strength properties and the absence of toxicity would find immediate application in the construction of protheses of medium or long duration for implantation purposes, or in the construction of elements of auxiliary machines for use in extracorporal circulation, such as renal dialysis apparatus or heart-lung machines.

For this purpose, materials could be used lying within a very wide range from aliphatic or aromatic polyamide polymers, polyesters, polycarbonates, polyurethanes and PVC to special metal alloys. Unfortunately, the use of these materials is strongly limited by their generally poor biocompatibility. This is because as soon as a foreign material is inserted into the blood circulation, it immediately gives rise to the formation of thrombi by the initiation of an extremely complicated process.

It is believed that there is firstly an adhesion of the blood platelets to the material surface, with the consequent release from the platelets of ADP and serotonin, which then cause platelet aggregation. The platelet aggregation is itself a fundamental stage in the formation of thrombi. This is because it gives rise to the release of phospholipids which are essential in the blood coagulation process, by promoting the conversion of fibrinogen into fibrin.

The role of ADP as a platelet aggregation inducer, and thus as an initiator of the thrombi formation process, is widely known. See for example the fundamental work of A. Gaarder and A. Hellem in Nature 192, 531 (1961). It is therefore apparent that the immobilisation of an enzyme such as apyrase able to convert into AMP and adenosine the ADP produced by the adhesion of the platelets to the surface of the material which is placed in contact with the blood can inhibit subsequent platelet aggregation, so blocking the formation of thrombi. In this respect, it has been found, and forms the subject matter of the present invention, that the immobilisation of apyrase on the surface of thrombogenic materials gives these latter satisfactory biocompatible properties.

These properties do not depend on the system used for immobilising the enzyme. This can be done by adsorption and subsequent cross-linkage on the surface of polymer materials, or even on metal surfaces, for example on the surface of needles used for the arterio-venous connections in extracorporal circulation.

Alternatively, the apyrase can be bonded covalently to functional groups present on the surface of materials of which the biocompatibility is to be increased. It is indeed possible, if necessary, to previously activate the material so as to release reactive groups on to its surface which can be used for immobilising the apyrase.

For example, the enzyme can be attached covalently to the amino (or carboxyl) groups of aliphatic or aromatic polyamides subjected to mild surface hydrolysis. In the same manner, carboxyl groups of surface-hydrolysed polyesters can be used.

The invention is described in detail by the following examples, which however are not to be considered limiting.

EXAMPLE 1

Nylon 6 rings (length 9 mm, inner diameter 4 mm, outer diameter 5 mm) were prepared, being careful during machining that the edges were chamfered and rounded.

A groove 0.25 mm deep was made along the middle of the outside of the ring over its entire circumference.

The rings were hydrolysed in 3.5 N HCl at 37° C. for 1 hour.

The fact that surface hydrolysis of the nylon had been carried out was confirmed by a colorimetric test made by immersing the rings, washed with water, in a solution containing 0.1% (weight-volume) of trinitrobenzenesulphonic acid in saturated tetraborate.

After about 1 hour, the formation of an orange coloration on the nylon surface confirmed that hydrolysis had taken place. At this point, the rings were immersed in a 2.5% glutaraldehyde solution, and were kept immersed for 3.5 hours at 4° C. The rings were then washed rapidly in iced water and immersed in a 0.01 N phosphate buffer solution containing 8 mg/ml of apyrase (specific activity 3.4 U.I./mg using ADP as substrate). The reaction was allowed to proceed at 4° C. for one day and one night. At the end of the reaction, the rings were washed in distilled water, and a test was made of enzymatic activity. One ring was immersed in 50 ml of a 0.1 M tris HCl buffer solution of pH 7.4 containing 0.25 mg/ml of ADP and 0.5 mg/ml of $CaCl_2$.

The mixture was kept stirring at 25° C. 1 ml samples were withdrawn at intervals of 30 minutes, and were analysed in order to determine inorganic phosphates following the method of Fiske and Subbarrow (C. H. Fiske; Y. Subbarrow; J. Biol. Chem. 66, 375 (1925)). An enzymatic activity of 4.5 $\mu$moles of inorganic phosphates released in one hour of reaction was measured on the rings.

The nylon rings with apyrase bonded covalently to the surface amino groups were subjected to an "in vivo" biocompatibility test by inserting them into the femoral vein of dogs of average size.

The insertion was made under general anaesthesia, and when the ring had been inserted into the vein it was fixed by means of a silk thread. The wound was sutured, and antibiotics were administered to the animal.

A similar untreated nylon ring was inserted for comparison purposes following the same procedure.

After an insertion period of 15 days, the rings were extracted and examined.

The ring with apyrase was found pervious, whereas the reference ring was completely occluded by thrombi.

A measurement made on the ring with apyrase extracted from the dog showed about 4 $\mu$moles of inorganic phosphates released in one hour.

EXAMPLE 2

Nylon 6 rings similar to those described in example 1 were prepared, and were immersed in a 0.01 M phosphate buffer solution of pH 7 containing 8 mg/ml of apyrase.

After 4 hours, a double volume of a 2.5% glutaraldehyde solution in a 0.01 M phosphate buffer solution at pH 7 was added.

The mixture was left to react at 4° C. for one day and one night. The rings were then washed and subjected to the test for enzymatic activity in accordance with the procedure described in example 1.

The enzymatic activity was found to be about 2 $\mu$moles of inorganic phosphates released in one hour by a single ring.

The "in vivo" biocompatibility test was carried out by inserting rings with apyrase and reference rings into the femoral vein of dogs of average size.

The method followed for these latter was as indicated in example 1. After an insertion period of 15 days, the rings were extracted. The ring with apyrase was found to be previous, and the measured enzymatic activity was equivalent to about 2 $\mu$moles of inorganic phosphates released in one hour.

The reference nylon ring was however completely occluded.

EXAMPLE 3

Polyethyleneterephthalate rings similar to those described in example 1 were prepared. The rings were hydrolysed in 1 M NaOH at 50° C. for 5 hours. The rings were then washed and immersed in 50 ml of a solution containing 8 mg/ml of apyrase and 10 mg/ml of N-ethyl-N'(3-dimethylaminopropylcarbodiimide) in a 0.1 M phosphate buffer at pH 6.8. The reaction was carried out at 4° C. for one night. In this manner the apyrase was bonded to the support by the formation of an amido bond between the $\epsilon$-aminolysine groups of the enzyme and the carboxyl groups of the surface-hydrolyzed polyester. The enzymatic activity test on the rings, carried out as indicated in example 1, gave values of approximately 4 $\mu$moles of inorganic phosphates released in one hour per ring. The "in vivo" biocompatibility test was carried out by inserting polyester rings with apyrase and non-treated rings into the femoral vein of experimental dogs. The method described in example 1 was followed. After 15 days of insertion, the rings were extracted. The reference ring was completely occluded, whereas the ring with apyrase was pervious with only some sporadic thrombi.

The enzymatic activity test on the ring after "in vivo" insertion indicated about 3 $\mu$moles of inorganic phosphates released in one hour.

EXAMPLE 4

Polyethyleneterephthalate rings similar to those described in example 1 were prepared. Apyrase was cross-linked to these rings following the procedure indicated in example 2. After immobilisation, the enzymatic activity per ring was found to be about 3 $\mu$moles of inorganic phosphates released in one hour. The "in vivo" biocompatibility test on dogs carried out following the method described in example 1 gave positive results for the rings with cross-linked apyrase, which were found to be pervious and almost completely free of thrombi, whereas the reference rings were found to be occluded. The residual enzymatic activity on the rings was about 2.5 $\mu$moles of inorganic phosphates released in one hour.

EXAMPLE 5

C 50 steel rings similar to those described in example 1 were prepared. Apyrase was fixed on to some of them by cross-linkage with glutaraldehyde by the procedure described in example 1. The activity immobilised on each ring was measured and found to be about 1.5 $\mu$moles of inorganic phosphates released in one hour. "In vivo" biocompatibility tests were carried out on experimental dogs as heretofore described.

After 15 days of insertion, the rings were extracted and examined. While the reference rings were found to be occluded, the rings with cross-linked apyrase were found to be open and with only slight thrombi on their inside. The residual activity on the rings treated with apyrase after insertion was found to be 0.9 $\mu$moles of inorganic phosphates released per hour.

We claim:

1. A method for preparing a non-thrombogenic apyrase-carrying prosthetic plastic material comprising the steps of hydrolytically activating the surface of a plastic material carrier selected from the group consisting of a polyamide polymer and a polyethylene terephthalate polymer, treating the hydrolyzed plastic carrier by immersing it into a buffered solution of a cross-linking agent selected from the group consisting of glutaraldehyde and N-ethyl-N'-(3-dimethylaminopropyl)carbodiimide and in a buffered solution of apyrase, and allowing said immersed plastic material carrier to stand for a time sufficient to effect the covalent bonding of apyrase to the surface of said plastic material carrier.

2. The method of claim 1 wherein said plastic material carrier is a polyamide and said hydrolysis is an acid hydrolysis.

3. The method of claim 1 wherein said plastic material carrier is polyethylene terephthalate, said hydrolysis is an alkaline hydrolysis, and said solution of a cross-linking agent is a buffered solution of N-ethyl-N'-(dimethylaminopropyl)carbodiimide, which solution is combined with said buffered solution of apyrase prior to the immersion therein of said hydrolytically-activated plastic material carrier.

4. Non-thrombogenic apyrase-carrying prosthetic plastic material articles prepared by the method of claim 1 consisting of plastic material from the group consisting of polyamides and polyethylene terephthalate having said apyrase covalently and permanently bonded on the surface thereof.

* * * * *